United States Patent
Noble

(10) Patent No.: US 7,634,379 B2
(45) Date of Patent: Dec. 15, 2009

(54) NEWTONIAN PHYSICAL ACTIVITY MONITOR

(75) Inventor: Christopher R. Noble, Winchester, MA (US)

(73) Assignee: Ultimate Balance, Inc., Winchester, MA (US)

(*) Notice: Subject to any disclaimer, the term of this patent is extended or adjusted under 35 U.S.C. 154(b) by 0 days.

(21) Appl. No.: 12/077,955

(22) Filed: Mar. 21, 2008

(65) Prior Publication Data

US 2008/0288200 A1    Nov. 20, 2008

Related U.S. Application Data

(60) Provisional application No. 60/930,749, filed on May 18, 2007, provisional application No. 60/934,216, filed on Jun. 11, 2007, provisional application No. 60/936,117, filed on Jun. 18, 2007.

(51) Int. Cl.
*G01P 15/00* (2006.01)
(52) U.S. Cl. ........................................... 702/141
(58) Field of Classification Search ............ 702/96, 702/141, 150–153, 176; 324/162; 600/595; 482/74

See application file for complete search history.

(56) References Cited

U.S. PATENT DOCUMENTS

| | | |
|---|---|---|
| 1,169,188 A | 1/1916 | Peck |
| 3,945,646 A | 3/1976 | Hammond |
| 4,353,375 A | 10/1982 | Colburn et al. |
| 4,502,035 A | 2/1985 | Obenauf et al. |
| 4,991,850 A | 2/1991 | Wilhlem |
| 5,074,302 A | 12/1991 | Poore et al. |
| 5,080,096 A | 1/1992 | Hooper et al. |
| 5,197,489 A | 3/1993 | Conlan |
| 5,221,088 A | 6/1993 | McTeigue et al. |
| 5,243,998 A | 9/1993 | Silverman et al. |
| 5,251,902 A | 10/1993 | Federowicz et al. |
| 5,253,870 A | 10/1993 | Bedney |
| 5,338,036 A | 8/1994 | Takeuchi et al. |
| 5,348,519 A | 9/1994 | Prince et al. |
| 5,372,365 A | 12/1994 | McTeigue et al. |
| 5,373,857 A | 12/1994 | Travers et al. |
| 5,430,435 A | 7/1995 | Hoch et al. |
| 5,524,894 A | 6/1996 | Shannon |
| 5,553,857 A | 9/1996 | Fish |
| 5,573,013 A | 11/1996 | Conlan |
| 5,592,401 A | 1/1997 | Kramer |
| 5,593,431 A | 1/1997 | Sheldon |
| 5,621,922 A | 4/1997 | Rush, III |
| 5,749,372 A | 5/1998 | Allen et al. |

(Continued)

FOREIGN PATENT DOCUMENTS

WO    WO 95/32666    12/1995

(Continued)

*Primary Examiner*—Bryan Bui
(74) *Attorney, Agent, or Firm*—Weingarten, Schurgin, Gagnebin & Lebovici LLP

(57) ABSTRACT

An improved apparatus and methods of posture and physical activity monitoring. The apparatus is physically mountable to or associated with an object or person, includes a multi-axis accelerometer, and derives measurements of posture and of acceleration. Methods are disclosed which provide improved estimations of posture, acceleration, energy expenditure, movement characteristics and physical activity, detect the influence of externally-caused motion, and permit automatic calibration of the apparatus in the field.

32 Claims, 8 Drawing Sheets

U.S. PATENT DOCUMENTS

| | | | |
|---|---|---|---|
| 5,788,655 A | 8/1998 | Yoshimura et al. |
| 5,836,829 A | 11/1998 | Van Cott et al. |
| 5,891,180 A | 4/1999 | Greeninger et al. |
| 5,895,328 A | 4/1999 | Pahio |
| 5,913,727 A | 6/1999 | Ahdoot |
| 5,916,181 A | 6/1999 | Socci et al. |
| 5,993,323 A | 11/1999 | Linenfelser |
| 6,032,530 A | 3/2000 | Hock |
| 6,038,074 A | 3/2000 | Kitaguchi et al. |
| 6,048,324 A | 4/2000 | Socci et al. |
| 6,059,576 A | 5/2000 | Brann |
| 6,095,991 A | 8/2000 | Krawsman et al. |
| 6,196,932 B1 | 3/2001 | Mrsh et al. |
| 6,254,513 B1 | 7/2001 | Takenaka et al. |
| 6,307,481 B1 | 10/2001 | Lehrman et al. |
| 6,331,168 B1 | 12/2001 | Socci et al. |
| 6,334,837 B1 | 1/2002 | Hein et al. |
| 6,356,856 B1 | 3/2002 | Damen et al. |
| 6,436,052 B1 | 8/2002 | Nikolic et al. |
| 6,449,508 B1 | 9/2002 | Sheldon et al. |
| 6,466,821 B1 | 10/2002 | Pianca et al. |
| 6,477,421 B1 | 11/2002 | Andersen et al. |
| 6,546,291 B2 | 4/2003 | Merfeld et al. |
| 6,568,396 B1 | 5/2003 | Anthony |
| 6,571,200 B1 | 5/2003 | Mault |
| 6,582,380 B2 | 6/2003 | Kazlausky et al. |
| 6,605,038 B1 | 8/2003 | Teller et al. |
| 6,611,783 B2 | 8/2003 | Kelly et al. |
| 6,658,292 B2 | 12/2003 | Kroll et al. |
| 6,678,549 B2 | 1/2004 | Cusimano et al. |
| 6,694,182 B1 | 2/2004 | Yamazaki et al. |
| 6,700,499 B2 | 3/2004 | Kubo et al. |
| 6,703,939 B2 | 3/2004 | Lehrman et al. |
| 6,730,047 B2 | 5/2004 | Socci et al. |
| 6,810,349 B2 | 10/2004 | Westerterp et al. |
| 6,819,247 B2 | 11/2004 | Birnbach et al. |
| 6,836,971 B1 | 1/2005 | Wan |
| 6,871,413 B1 | 3/2005 | Arms et al. |
| 6,937,900 B1 | 8/2005 | Pianca et al. |
| 6,997,882 B1 | 2/2006 | Parker et al. |
| 7,054,687 B1 | 5/2006 | Andersen et al. |
| 7,145,461 B2 | 12/2006 | Lehrman et al. |
| 7,198,607 B2 | 4/2007 | Jamsen |
| 7,204,145 B2 | 4/2007 | Heinkes et al. |
| 7,237,446 B2 | 7/2007 | Chan et al. |
| 7,255,437 B2 | 8/2007 | Howell et al. |
| 7,328,612 B2 | 2/2008 | Jamsen et al. |
| 7,334,472 B2 | 2/2008 | Seo et al. |
| 7,383,728 B2 | 6/2008 | Noble et al. |
| 7,555,398 B2 * | 6/2009 | Fowler ............... 702/104 |
| 2001/0032059 A1 | 10/2001 | Kelly, Jr. et al. |
| 2002/0060633 A1 | 5/2002 | Crisco, III et al. |
| 2002/0077189 A1 | 6/2002 | Tuer et al. |
| 2002/0077570 A1 | 6/2002 | McLeod et al. |
| 2002/0116147 A1 | 8/2002 | Vock et al. |
| 2002/0123386 A1 | 9/2002 | Permutter |
| 2002/0134153 A1 | 9/2002 | Grenlund |
| 2002/0173364 A1 | 11/2002 | Boscha |
| 2002/0173365 A1 | 11/2002 | Boscha |
| 2002/0183657 A1 | 12/2002 | Socci et al. |
| 2002/0187860 A1 | 12/2002 | Shoane |
| 2003/0028377 A1 | 2/2003 | Noyes |
| 2003/0116166 A1 | 6/2003 | Anthony |
| 2003/0135129 A1 | 7/2003 | Cusimano et al. |
| 2003/0138763 A1 | 7/2003 | Roncalez et al. |
| 2003/0144088 A1 | 7/2003 | Shoane |
| 2003/0163287 A1 | 8/2003 | Vock et al. |
| 2003/0207718 A1 | 11/2003 | Perlmutter |
| 2003/0216228 A1 | 11/2003 | Rast |
| 2004/0001373 A1 | 1/2004 | Liaw et al. |
| 2004/0006747 A1 | 1/2004 | Tyler |
| 2004/0008427 A1 | 1/2004 | Nattermann et al. |
| 2004/0010390 A1 | 1/2004 | Kelly, Jr. et al. |
| 2004/0014531 A1 | 1/2004 | Ziener-Gundersen |
| 2004/0033843 A1 | 2/2004 | Miller, IV et al. |
| 2004/0077438 A1 | 4/2004 | Choi |
| 2004/0259651 A1 | 12/2004 | Storek |
| 2005/0046576 A1 | 3/2005 | Julian et al. |
| 2005/0288119 A1 | 12/2005 | Wang et al. |
| 2006/0150734 A1 | 7/2006 | Mimnagh-Kelleher et al. |
| 2006/0184336 A1 | 8/2006 | Kolen |
| 2006/0259268 A1 | 11/2006 | Vock et al. |
| 2006/0284979 A1 | 12/2006 | Clarkson |
| 2007/0118056 A1 * | 5/2007 | Wang et al. ............... 600/595 |
| 2007/0124075 A1 | 5/2007 | Lee et al. |
| 2007/0193352 A1 | 8/2007 | Heinks et al. |

FOREIGN PATENT DOCUMENTS

| | | |
|---|---|---|
| WO | WO 98/24242 | 6/1998 |
| WO | WO 99/18657 | 4/1999 |
| WO | WO 99/21477 | 5/1999 |
| WO | WO 99/26704 | 6/1999 |
| WO | WO 00/17615 | 3/2000 |
| WO | WO 01/50957 | 7/2001 |
| WO | WO 01/66006 | 9/2001 |
| WO | WO 02/076293 | 10/2002 |
| WO | WO 02/093272 | 11/2002 |
| WO | WO 02/102475 | 12/2002 |
| WO | WO 03/029745 | 4/2003 |
| WO | WO 03/061779 | 7/2003 |
| WO | WO 03/068339 | 8/2003 |
| WO | WO 2004/008427 | 1/2004 |

* cited by examiner

NEWTONIAN PHYSICAL ACTIVITY MONITOR

CROSS REFERENCE TO RELATED APPLICATIONS

This application claims benefit of U.S. Provisional Patent Application No. 60/930,749 filed May 18, 2007 entitled PHYSICAL ACTIVITY MONITOR, U.S. Provisional Patent Application No. 60/934,216 filed Jun. 11, 2007 entitled PHYSICAL ACTIVITY AND POSTURE MONITOR, and U.S. Provisional Patent Application No. 60/936,117 filed Jun. 18, 2007 entitled PHYSICAL ACTIVITY AND POSTURE MONITOR.

STATEMENT REGARDING FEDERALLY SPONSORED RESEARCH OR DEVELOPMENT

Not applicable

BACKGROUND OF THE INVENTION

The present invention relates generally to the field of physical activity monitoring, and more specifically to apparatus and methods of monitoring and measuring posture and physical activity using acceleration data for research, training, monitoring, sports, leisure, therapeutic and rehabilitation purposes.

Uni-axial and tri-axial accelerometers have been used for many years in wearable devices that estimate physical activity. The tri-axial devices provide acceleration data for three orthogonal axes, plus the vector magnitude.

Many conventional systems integrate the accelerometer data over a time window (an "activity count"), and use linear or higher-order formulas or look-up tables to estimate Energy Expenditure (EE), expressed in units such as METS (multiple of basal metabolic rate), or calories. The offset and scaling factors of the conversion equations are often determined by statistical curve-fitting, using population-sample accelerometer data collected concurrently with reference EE measurements, such as from oxygen consumption or doubly-labeled water.

The applicant has recognized that existing systems have shortcomings, including one or more of the following:

1) Existing systems do not monitor both the intensity of the physical activity of the user and his/her posture.

2) Since the accelerometer senses the combination of the effects of gravity and acceleration, either a high-pass accelerometer sensor (such as some piezoelectric sensors) or a high-pass filter after a wideband DC sensor (such as a suspended proof-mass MEMS accelerometer) is used to suppress the gravity signal. However, this filtering method does not accurately suppress the gravity signal for the following two reasons: (a) the wearer's posture can change during the measurement, creating an AC component to the sensed gravity signal that can feed through the high-pass filter, and (b) for many daily-living situations, the gravity signal is much stronger than the acceleration signal, and it is difficult to accurately filter out a strong signal from a weak one.

3) Existing systems that use a low-pass filter to suppress the acceleration signal perform the filtering function on both the direction and magnitude of the raw signal. This leads to inaccuracies in the resulting calculation of acceleration, as the filter can allow feed-through of either component of the raw signal in either or both directions.

4) Existing systems which subtract a calibrated value of gravity from the total signal to determine the magnitude of acceleration do not correct the calculation for differences in direction between gravity and the user's acceleration, causing errors in the resulting value of acceleration.

5) Accelerometer sensor accuracy cannot be monitored or adjusted in the field without periodic calibration that requires user manipulation and interrupts data capture.

6) Existing systems require precise attachment, aligned with the wearer's vertical, anterior-posterior, or medio-lateral axes, and do not correct for alignment errors between the sensor axes and those of the wearer, or for changes in the alignment during the measurement process, or for changes in the wearer's posture during the measurement process.

7) Existing systems do not have a means to automatically detect the influence of modes of conveyance such as elevators, automobiles, or airplanes on measured acceleration.

8) Existing systems correlate step counts or total dynamic acceleration (either uni-axial, tri-axial vector, or tri-axial sum-of-axes) to Energy Expenditure (EE), and do not discriminate between physical activity related to changes in potential energy ($EE_P$, i.e. displacement against gravity), and physical activity related to changes in kinetic energy ($EE_K$, i.e. acceleration against inertia). Since the relationships between acceleration and these two types of energy are different, this leads to measurement errors. In addition, separate measures of these two types of physical activity can be useful for purposes of monitoring, analysis, and feedback to the user.

9) Existing systems assume a fixed ratio between vertical and horizontal Energy Expenditure.

10) Existing systems analyze the frequency or pattern of acceleration to estimate activity levels. However, pattern analysis is prone to misinterpretation, especially in daily-living situations where movements can be complex and unpredictable.

11) Existing systems use multiple accelerometers in different orientations, and determine which accelerometer is most favorably aligned with the wearer's motion during a sampling interval. However, there are many situations where no single accelerometer is exactly aligned.

12) Existing systems use other positional sensors in addition to a single multi-axis linear accelerometer, such as rotational (gyroscopes or additional accelerometers), magnetic, or locational sensors (GPS or altimeter), or physiological sensors, such as heart-rate, muscular activity, ventilation (breathing), or skin-temperature sensors, to improve the measurement of posture or activity. However, the addition of these other sensors increases the cost and complexity of the system, and makes it difficult to incorporate the system as software into a device such as a cell phone or wearable music player, which already incorporates a single multi-axis accelerometer but not these other sensor types.

It would therefore be desirable to have improved apparatus and methods of monitoring and measuring posture and physical activity using multi-axis accelerometer sensors that would avoid the drawbacks of the above-described conventional systems.

BRIEF SUMMARY OF THE INVENTION

In accordance with the present invention, an improved system and method of acquiring and/or processing data to monitor and measure posture and intensity of physical activity is disclosed. In one embodiment, an apparatus for simultaneously monitoring the posture and acceleration of an object includes a 3-axis sensor, a memory, and at least one processor. The apparatus is configured to be attached to, held against, inserted into, or otherwise physically associated with the object to be monitored. The 3-axis sensor is configured to sense apparent acceleration along each of a first axis, a second axis, and a third axis. The memory is operative to store data representing the sensed magnitudes of apparent acceleration along each of the three axes, and the processor is operative to process the data stored in the memory. Specifically, the processor uses a method to estimate both the actual gravity vector and the acceleration vector based upon the sensor signals. In this way, the apparatus provides two separate time-based streams of data that can be used individually or together to accurately determine the type and intensity of physical activity, and for any other suitable purpose.

In another embodiment, the acceleration data and the posture data are used to calculate one or more of the total EE, $EE_P$, and $EE_K$ of the system.

In another embodiment, $EE_K$ in a plurality of directions are distinguished from each other.

In another embodiment, posture data, acceleration data, EE, $EE_K$, $EE_K$ in one or more directions, $EE_P$, and other inputs are used alone or in combination to evaluate activity patterns, determine activity types, or to evaluate movement efficiency, physical impairment or for other diagnostic, rehabilitative or training purposes.

In another embodiment, the accuracy of the estimation of posture and acceleration is improved by use of a feedback loop whose control signals are measures of quality derived from the posture and acceleration outputs.

In another embodiment, sensor errors are measured by analyzing the system outputs when the user is determined to be at rest.

In another embodiment, the acceleration sensors are offset to correct the sensor errors, or to compensate for the effect of gravity, e.g., in order to make optimal use of the dynamic range of the A/D converter, or for any other suitable system design purposes.

In other embodiments, one or more of the above-described features may be implemented in whole or in part in software and incorporated into devices such as cell phones, personal digital assistants (PDAs), personal music players, special purpose monitoring devices, implanted medical devices such as pacemakers, or any other suitable portable, wearable, or insertable device, and may make use of existing hardware or software features of the device to implement portions of the activity and posture monitoring system.

The various elements may be included in a single housing, or distributed among a plurality of housings, with suitable functional wired or wireless inter-housing communication, or incorporated into articles to be worn such as apparel or clothing, or eyeglasses, sunglasses, wristwatches, or any other suitable accessories.

Other features, functions, and aspects of the invention will be evident from the Detailed Description of the Invention that follows.

BRIEF DESCRIPTION OF THE SEVERAL VIEWS OF THE DRAWINGS

The invention will be more fully understood with reference to the following Detailed Description of the Invention in conjunction with the drawings of which:

FIG. 6b is a geometric representation of the magnitude of the runner's Kinetic Energy Expenditure ($EE_K$) that is sensed and calculated by the system of FIG. 1, for various horizontal directions relative to the axes shown in FIG. 6a.

DETAILED DESCRIPTION OF THE INVENTION

The disclosures of U.S. Provisional Patent Application No. 60/930,749 filed May 18, 2007 entitled PHYSICAL ACTIVITY MONITOR, U.S. Provisional Patent Application No. 60/934,216 filed Jun. 11, 2007 entitled PHYSICAL ACTIVITY AND POSTURE MONITOR, and U.S. Provisional Patent Application No. 60/936,117 filed Jun. 18, 2007 entitled PHYSICAL ACTIVITY AND POSTURE MONITOR, are incorporated herein by reference in their entirety.

The definitions below are provided for purposes of illustration, not limitation, in order to assist with understanding the discussion that follows.

Activity type: "Activity type" is a qualitative description of physical activity, e.g., walking, running, swimming, vacuuming floors, washing dishes, climbing stairs, etc.

Energy Expenditure: "Energy Expenditure (EE)" is a measure of the amount of energy that is expended during the physical effort required to perform an activity. For example, EE can be expressed in footsteps (an inaccurate measure), calories of metabolic activity (a more accurate measure), or any other suitable units of expended energy. For purposes of this disclosure, EE includes activity-related energy expenditure, but does not include basal or dietary metabolic activity.

Figure 3:
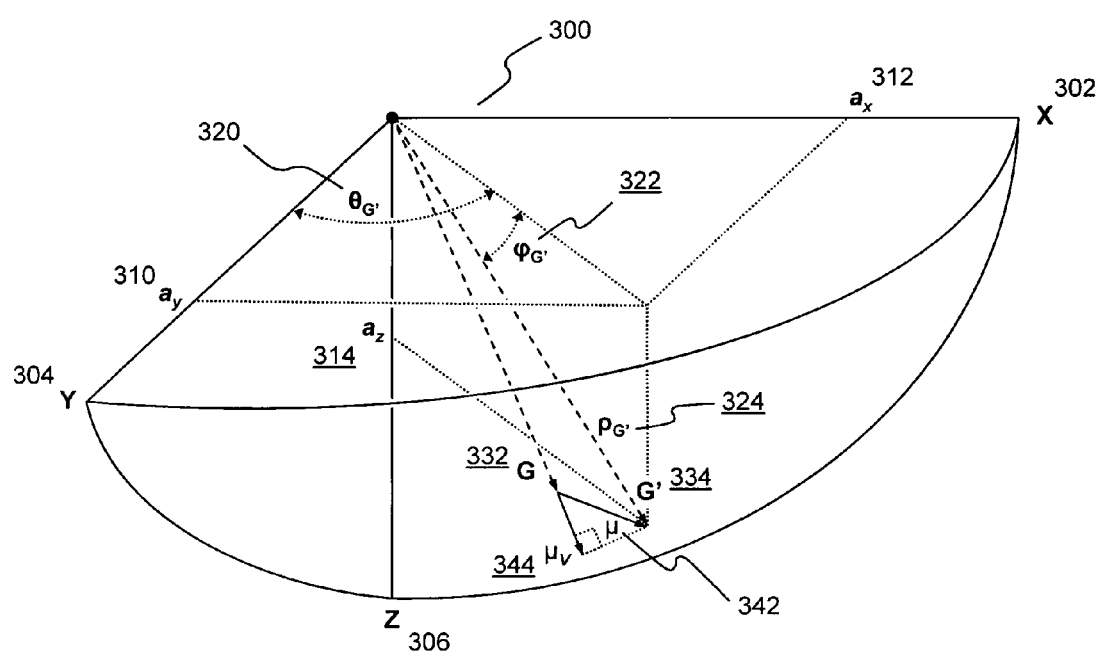
FIG. 3 is geometric model of the posture and acceleration signals that are sensed and calculated by the system of FIG. 1.

Posture: The "posture" of an object or person is the direction and magnitude of the tilt of the object or person in 3-dimensional space, relative to a reference direction in the horizontal plane. For example, as shown in FIG. 3, angles $\theta_{G'}$ 320 and $\phi_{G'}$ 322 associated with an exemplary apparent gravity vector G' 334 define the posture of an object or person aligned with the orientation of G' 334, relative to direction Y 304 in the XY plane. The posture of an individual is often meant to refer to the posture of the individual's spine, but can refer to the posture of the head or of an extremity.

Activity monitoring: "Activity monitoring" can include capturing data indicative of either the activity type or the EE or both. One example of data indicative of activity type is upper body posture over time. Posture data can provide useful information in activity monitoring: e.g., whether an individual is recumbent or upright, during what time intervals, and at what times of day or night. Patterns of posture data can also be combined with patterns of measured EE for more complete activity monitoring.

Acceleration: "Acceleration" is the direction and magnitude of the acceleration of a user. References to a user may constitute references to a person or object being monitored.

Apparent gravity: "Apparent gravity" refers to the total measurement made by a sensor that is sensitive to the sum of acceleration and gravity, e.g., an accelerometer.

Gravity vector or actual gravity vector: "Gravity vector" or "actual gravity vector" is a vector representing the gravity that is felt by an object, relative to a reference frame of the object. Since the gravity vector on earth always points towards the center of the earth, and is thus normal to the horizontal plane, changes in the direction of the gravity vector relative to a reference frame of the object result from changes in posture of the object. It is assumed in the embodiments described in this application that the object is at sea level on earth, and that the length of the gravity vector is "standard gravity", i.e., 1 g≈9.8 m/sec². Corrections for other locations can be made using techniques known in the art.

Component of a vector: A "component" of a first vector refers to a second vector which can be added to a third vector to equal the first vector. In FIG. 3, vectors G 332 and μ 342 are components of vector G' 334.

Characteristic of a vector: A "characteristic" of a vector refers to the direction or magnitude of the vector, or to a statistic (such as the average value over a time interval) of the characteristic. In FIG. 3, $\theta_G'$ 320, $\phi_G'$ 322, and $\rho_G'$ 324 are characteristics of vector G' 334.

Potential Energy Expenditure ($EE_P$): "Potential Energy Expenditure" $EE_P$ is that portion of EE that is related to changes in vertical position that are resisted by gravity.

Kinetic Energy Expenditure ($EE_K$): "Kinetic Energy Expenditure" $EE_K$ is that portion of EE that is related to acceleration in any direction, which is resisted by the inertia of the object.

Affected Mass (M): "Affected mass" M is the mass of the body or body part of a person and objects to which the device is attached and to which the motion-related energy expenditure is applied. One example is the case of a single device used to measure the caloric expenditure of a runner wearing weights, for which M is the total mass of the runner and the weights. Another example is the use of multiple sensors on the trunk and extremities, to more accurately measure the energy expenditure in those different parts of the body, for which the total mass of the wearer is distributed among energy-expenditure formulas applied to the outputs of each of the respective sensors. For purposes of this disclosure, no distinction is made between mass and weight.

Figure 1:
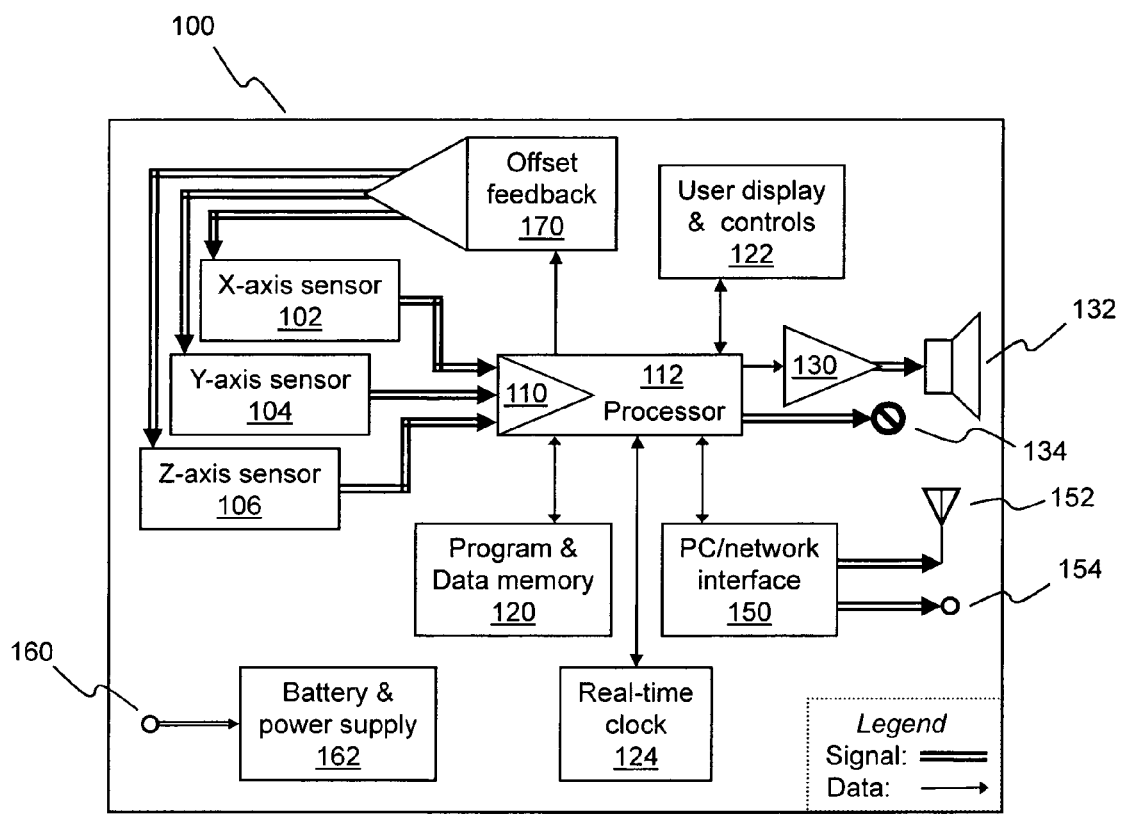
FIG. 1 is a block diagram of an exemplary embodiment of a system operative in accordance with the present invention.

FIG. 1 depicts an illustrative embodiment of a physical activity monitoring device 100, in accordance with the present invention. The physical activity monitoring device 100 provides proper operation and accuracy when physically associated in substantially any direction and orientation relative to the user. In addition, the device 100 provides visible, audible (e.g., alarms, tones, human speech), and/or tactile feedback to the user.

In one embodiment, the physical activity monitor 100 includes an X-axis sensor 102, a Y-axis sensor 104, a Z-axis sensor 106, a signal multiplexer and analog-to-digital converter (A/D) 110, a data processor 112, a program and data memory 120, a user display and controls 122, a real-time clock 124, an audio output converter 130, a speaker 132, one or more tactile vibration outputs 134, a PC/network interface 150, a wireless networking antenna 152, a wired networking connector 154, a battery charger connector 160, and a battery and power supply 162. The data processor 112 may selectively power down functional components during idle periods, such as powering down the sensors 102, 104, 106 between samples, to conserve power. When charging, the battery charger connector 160 is connected to a battery charger (not shown). When in a network configuration, the PC/network interface 150 is connected to a personal computer (PC; not shown), or a local area network (LAN), a wide area network (WAN), or any other suitable network, through either the wireless networking antenna 152 or the wired networking connector 154.

The physical activity monitor 100 also includes an offset feedback function 170, which offsets the outputs of the sensors 102, 104, 106 before conversion by the A/D converter 110 to correct for calibration errors, and to offset the sensors for the effect of gravity. After conversion by the A/D converter 110, the dynamic range of each of the digital sensor outputs corresponding to the analog sensor outputs is determined at least in part by the adjusted offset of the respective analog output. Each of the sensor outputs is individually offset by a respective offset signal generated by the offset feedback function 170, which is in turn controlled by the processor 112, and can be implemented in hardware, in a mix of hardware and software, or entirely in software by using the A/D 110 with a sufficiently wide input range to accommodate the entire range of excursions of signals from the sensors 102, 104, 106 without feedback, and by offsetting the sensor signals in software after A/D conversion.

It is noted that alternative embodiments of the physical activity monitoring device 100 may include a subset of the functional components illustrated in FIG. 1. It is also noted that in the presently disclosed embodiment, the X, Y, and Z-axis sensors 102, 104, 106 are accelerometers oriented within the device 100 so that their respective sensitive axes, namely, the X-axis 302, the Y-axis 304, and the Z-axis 306 (see FIG. 3), are positioned at 90° relative to one another. In other embodiments, the X, Y, and Z-axis sensors may employ any other suitable technique for sensing gravity and acceleration, and may be oriented at any other suitable angle relative to one another.

For example, each of the X, Y, and Z-axis sensors 102, 104, 106 may be a suspended proof-mass MEMS accelerometer such as the ADXL103 device sold by Analog Devices Inc., Norwood, Mass., U.S.A. Alternatively, the X, Y, and Z-axis sensors 102, 104, 106 may be implemented using a single three-axis accelerometer such as the ADXL330 device sold by Analog Devices Inc. Alternatively, any other suitable set of accelerometers may be used. The outputs of the accelerometers are coupled to the multiplexer-A/D converter 110 to produce digitized accelerometer data for processing by the processor 112.

The X, Y, and Z-axis sensors 102, 104, 106 sense gravity and acceleration along the X, Y, and Z axes 302, 304, 306, respectively, by measuring the projection of the apparent gravity vector G' 334 on their respective axes that is the sum of gravity G 332 at the location of the device 100 and the acceleration p 342 (see FIG. 3) of the device 100.

The outputs of the X, Y, and Z-axis sensors 102, 104, 106 can be filtered in the analog or digital domain using any suitable hardware or software components to reject noise or signals at frequencies beyond those of interest for an intended application. For example, autogenous human trunk movement occurs at frequencies less than approximately 10 Hz. Filtering and sampling of outputs of the sensors 102, 104, 106 can be designed to ensure that relevant motion data can be captured without attenuation or aliasing. Additionally, data samples can be aggregated to reduce data storage requirements.

The PC/network interface 150 may be a wired or wireless (e.g., infrared or RF) interface for downloading or uploading data to or from the program and data memory 120 and the real-time clock 124. The PC/network interface 150 may also be configured for controlling the device 100 remotely. Time stamps generated by the real-time clock 124 and sequences of measurements performed by the device 100 and stored within the program and data memory 120 may be used for local processing, for feedback to the user, and for uploading to a computer via the PC/network interface 150. In addition, application-specific audible feedback phrases, measurement algorithms, cueing sequences, and other data may be downloaded to the device 100 from a computer or over a communications network such as the Internet.

The physical activity monitoring device 100 may also be configured to provide user cueing, including motivational or interrogative feedback in the form of alarms, tones, audible phrases stored in the program and data memory 120 or synthesized or otherwise created by the device. The audible user feedback phrases may be constructed and selected by the device 100 under user control or under control of the data processor 112, which may sequence the selected alarms, tones, or phrases in response to user motions, postures, or activity monitored by the device.

In addition, the physical activity monitoring device 100 may be configured to provide performance feedback to the user that is contextual to a specific application. For example, the system may provide progress against objectives to the user at certain times of day, upon completion or lack thereof of milestones, or upon request by the user.

Figure 2:
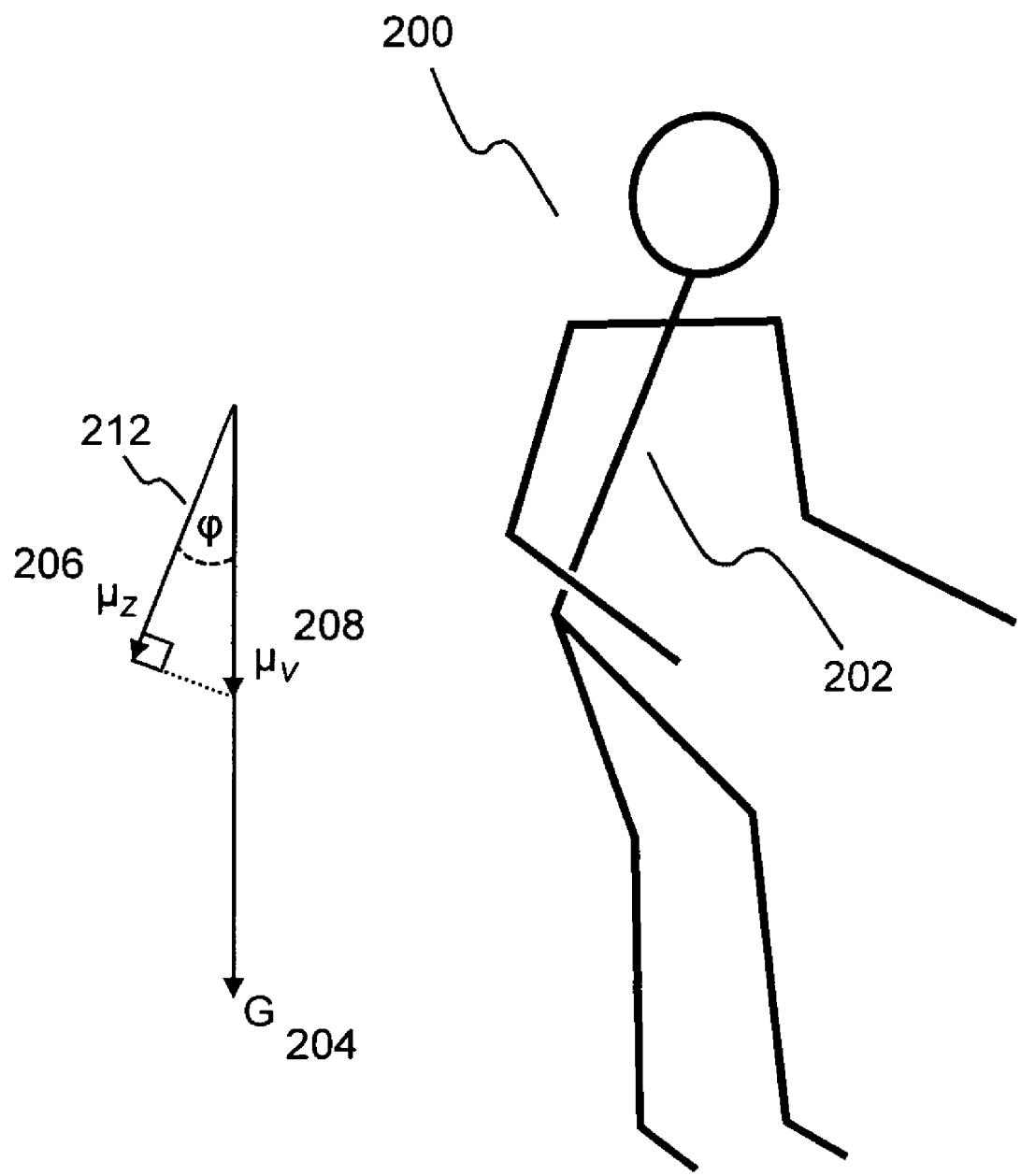
FIG. 2 is an illustration of certain force vectors and their relationships to the posture of a typical user.

FIG. 2 is an illustration of certain vectors and their relationships to the posture of a representative user 200. The vertical acceleration $\mu_v$ 208 of the torso 202 of the user can be directly measured by a uni-axial accelerometer attached to and aligned with the user's torso, if the accelerometer is pointing in the vertical direction, as shown by the direction of the gravity vector G 204. However, if the accelerometer is aligned with the user's torso 202 but the torso is leaning at an angle $\phi$ 212, then the accelerometer will measure $\mu_z$ 206 instead of the actual vertical acceleration $\mu_v$ 208, where $\mu_z$ is the projection of $\mu_v$ on the torso's axis. Conventional activity monitors that measure vertical acceleration do not take into account the angle $\phi$, and thus cannot compensate for the effect of $\phi$ and of changes in $\phi$ on the measured vertical acceleration. A similar error is introduced into measures of horizontal acceleration.

FIG. 3 is a geometric model 300 that illustrates the data format and operation of one embodiment of the physical activity monitoring device 100. Specifically, the geometric model 300, which is constructed with reference to both the spherical and Cartesian coordinate systems, may be used to quantify changes in the posture of the person or object to which the device is attached, and acceleration in the various directions relative to the horizontal plane. The geometric model 300 includes an entire unit sphere, of which only one octal portion is shown for clarity. The radius of the sphere is equal to 1 g, i.e., the magnitude of gravity on Earth. X-axis 302 represents the sensitive axis of the X-axis sensor 102, Y-axis 304 represents the sensitive axis of the Y-axis sensor 104, and Z-axis 306 represents the sensitive axis of the Z-axis sensor 106. In addition, FIG. 3 depicts one possible direction of an exemplary apparent gravity vector G' 334, where G' is the sum of the actual gravity vector G 332 and of the acceleration vector $\mu$ 342. Because G always points in the same direction, i.e., toward the center of the earth, the device 100 can determine changes in the posture and acceleration of the person or object to which it is attached by decomposing changes in the apparent gravity vector G' into its component parts, G and $\mu$.

It is noted that the length of the vector G is equal to 1 g, i.e., the radius of the unit sphere, and that G' and $\mu$ can be of any length and direction relative to G. It is also noted that use of the spherical coordinate system is for illustrative purposes only, and that all of the inputs, outputs, and formulas expressed herein can be represented and expressed in any other suitable coordinate system.

Within the geometric model 300, direction ($\theta_{G'}$ 320 and $\phi_{G'}$ 322) and magnitude $\rho_{G'}$ 324 of the apparent gravity vector G' 334 can be determined by applying known trigonometric formulas to the outputs $a_x$ 312, $a_y$ 310, and $a_z$ 314 of the X-axis, Y-axis, and Z-axis sensors sampled quasi-simultaneously.

Methods of distinguishing the acceleration ($\mu$) of device 100 from its posture (G) are described below with reference to FIG. 4. In a first variation on this method, feedback is not used and blocks 414 and 450 are not required. Signals representing the angles $\theta_{G'}$ (402 & 320) and $\phi_{G'}$ (404 & 322) are filtered by filter components 410 and 412 respectively, to suppress just the effects of the acceleration vector $\mu$ 342 from the apparent gravity vector G' 334.

Filter components 410 and 412 may be low-pass, band-pass, high-pass or combinations thereof, may be sampled or continuous, may use any suitable architecture such as finite-impulse response (FIR), infinite-impulse response (IIR), and frequency domain (such as Discrete Cosine Transform (DCT) or Fast Fourier Transform (FFT)), and may use any suitable synthesized technique such as look-ahead, predictive, wavelet, or Kalman filtering. Further, any suitable filter architectures and values for the filter components 410 and 412 can be chosen to perform this step if there are known differences between the characteristic variations of G and $\mu$. For example, if the majority of the magnitude variation of the acceleration vector $\mu$ is in a sufficiently higher frequency band than the directional variation of the posture, i.e., of the actual gravity vector G, then a 15-tap, 0.5 Hz FIR low-pass filter with a 6 Hz sampling rate will attenuate a periodic acceleration vector $\mu$ with a period of 1 second by 33 dB, while attenuating a periodic G with a period of 9 seconds by less than 1 dB.

Figure 4:
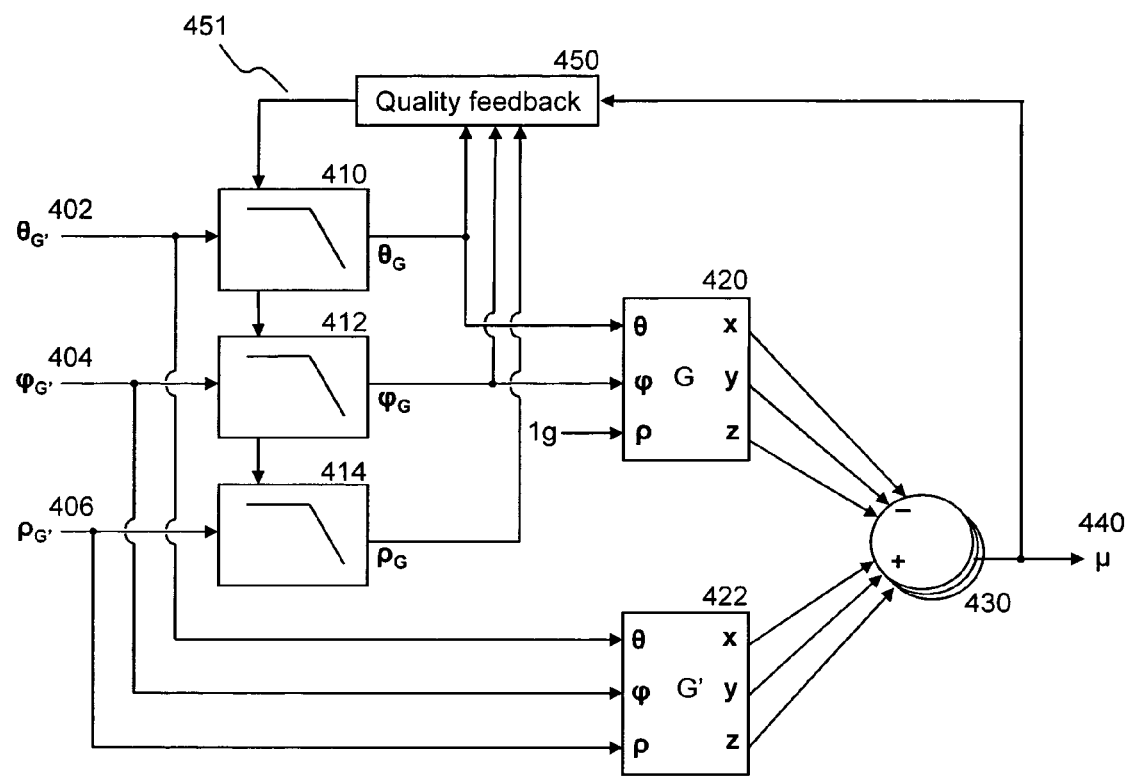
FIG. 4 is a schematic diagram of a method to discriminate between posture and acceleration in the system.

The previous example improves on those conventional systems that filter out the G signal from the $\mu$ signal, by instead filtering out the effect of $\mu$ on the direction of G, imposing a 1 g length to G, and determining $\mu$ arithmetically (see FIG. 4). In many applications, G is considerably stronger than $\mu$ and varies in direction over a lower frequency band and range, and thus the presently disclosed embodiment provides a more accurate output. Additionally, the constant and known length of G ($\rho_G$=1 g) is used in the presently disclosed embodiment to further refine the measurement process, and for other purposes such as calibrating the sensors during use.

As shown in FIG. 4, the filters 410 and 412 generate output signals corresponding to angles $\theta_G$ and $\phi_G$, respectively, which define the actual gravity vector G. Next, assuming that $\rho_G$=1 g, signals representing the angles $\theta_G$ and $\phi_G$ and the known value 1 g of the length $\rho_G$ of G are converted to Cartesian coordinates by the converter 420. Similarly, the signals representing the angles $\theta_{G'}$ 402 and $\phi_{G'}$ 404, and the length $\rho_{G'}$ 406, are converted to Cartesian coordinates by the converter 422. Finally, a representation of the acceleration vector $\mu$ 440 is obtained at a summation node 430 by subtracting the actual gravity vector G from the apparent gravity vector G'.

In a variation on this method, a filter control signal 451 is used to optimize the filters 410 and 412, with the optional addition of a filter 414 and a feedback function 450. In this variation, the characteristics of the filters 410, 412 and 414 are adjusted by the filter control signal 451 to minimize deviations from target values of characteristics of G and $\mu$. For example, target values in some applications could be $\rho_G$=1 and avg($\rho_\mu$)=0, since the magnitude of the gravity vector is a constant, 1 g, and the average acceleration of a human body performing physical activity is zero if its velocity tends towards a constant value. In such applications, an example of an optimization rule could be to reduce the bandwidth of low-pass filters 410, 412, and 414 if $\rho_G \neq 1$ (feed-through of $\mu$ into G), and increase the bandwidth if avg($\rho_\mu$)$\neq$0 (feed-through of G into μ). In other variations on this method, components of G or μ, such as the vertical component of μ, can be optimized.

It is noted that in some applications, a delay can occur between data acquisition and required output to the user. This can allow a range of recursive, successive-approximation or look-ahead filters, or signal synthesis techniques, to be used in variations of this method. For example, in cases where the frequency band of variations in G and μ overlap, the filters 410, 412, and 414 can be implemented as signal synthesizers, and synthesize an approximation of G with a first constraint of $\rho_G=1$. The approximate G sequence can then be optimized recursively until average($\rho_\mu$)=0. An additional exemplary quality metric is that μ often oscillates along a stable direction and its inverse over several cycles when the user is active in physical exercise.

A method to calibrate the accuracy of the X, Y, and Z sensors and the signal path through the multiplexer-A/D converter 110 is described below, with reference to FIGS. 1, 3, and 5. For an individual engaged in typical activities, immobility of the unit for more than several seconds is significant and indicative that the unit has been removed or that the user is in a resting (not necessarily supine) position, and thus G is equal to 1 g and μ is equal to 0. These periods can be determined by the lack of significant change in values of the direction ($\theta_{G'}$ and $\phi_{G'}$) and length ($\rho_{G'}$) of G'. During these periods, the gain and/or offset of the X, Y, and Z-axis sensors 102, 104, and 106 can be adjusted to zero out the error in the computed value of $\rho_G$. Any suitable calibration rule(s) can be applied based on sensor characteristics and the initial factory calibration of the system. For example, the ADXL330 (Analog Devices, Inc.) exhibits almost no gain error or drift over time or temperature when referenced to the power supply. The offsets of the three channels, however, can vary and drift significantly, but the drift slopes can be characterized in an initial calibration process and a weighted correction can be applied to each axis during each field-calibration opportunity. During periods of immobility, the accelerometer sample rate can also be reduced to conserve battery power.

Figure 5:
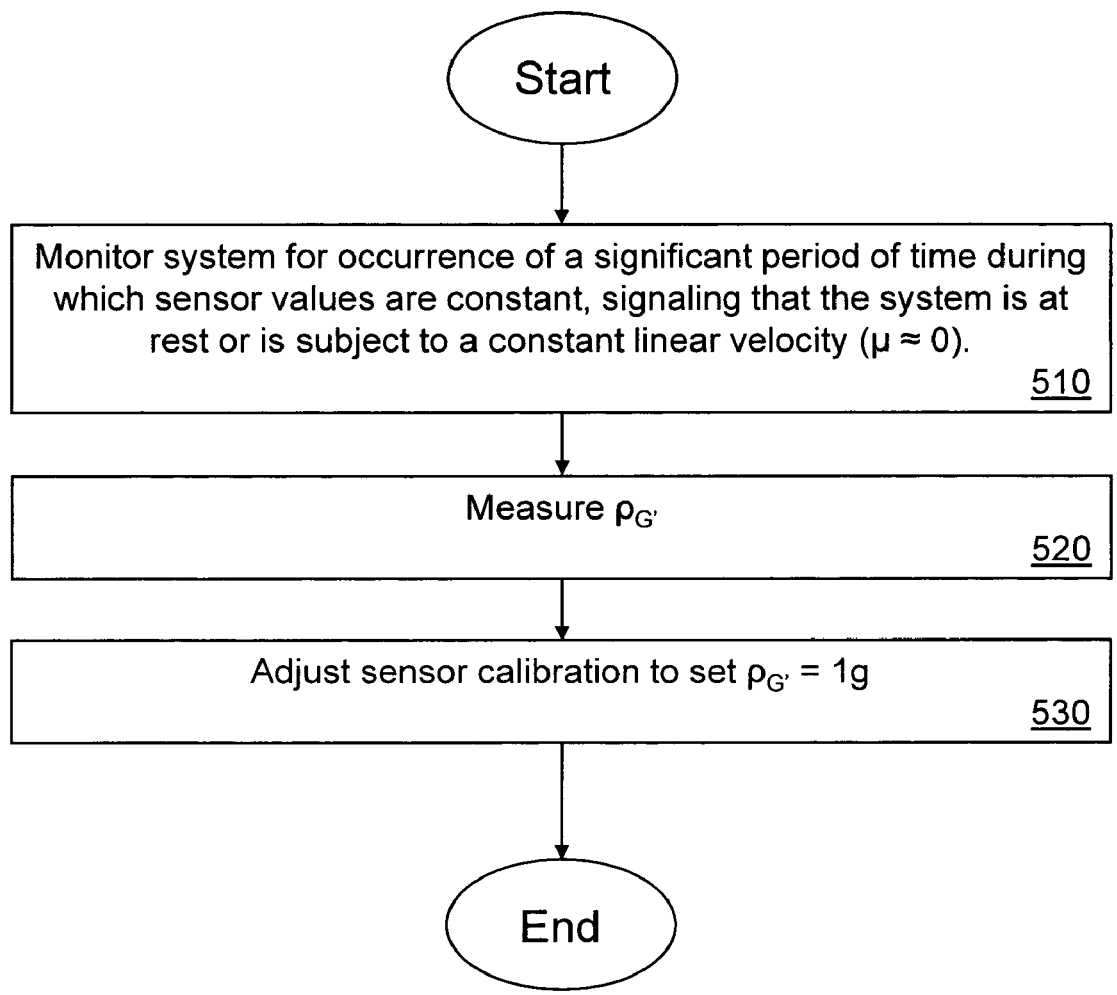
FIG. 5 is a flow diagram of a method of calibrating the input sensors automatically based on activity and posture patterns.

FIG. 5 is a flow diagram depicting the operation of a system, in accordance with the present invention, which recalibrates the accelerometers when the system is at rest (e.g., when the user is immobile or has removed the system). This ensures that the accuracy of the accelerometers and A/D is maximized, and also serves as a periodic diagnostic on the proper operation of the system. As depicted in step 510, the system is monitored for occurrence of a significant period of time (e.g., several seconds) during which sensor values are constant, i.e., substantially unchanging, signaling that the system is at rest or is subject to a constant linear velocity (μ≈0). Specifically, the multi-axis sensor measures the apparent gravity vector G', during a specified time interval, to obtain a plurality of substantially unchanging samples of G'. Next, as depicted in step 520, using the samples of G', the magnitude $\rho_{G'}$ of G' is measured. The sensor calibration is then adjusted to set $\rho_{G'}$ to 1 g.

In a variation of this calibration method, the user can be instructed to place the device in one or more reference positions, or to manipulate the device through a sequence of movements and/or rotations, and the values of calibration adjustments can be determined by monitoring changes in values of the direction ($\theta_{G'}$ and $\phi_{G'}$) and/or length ($\rho_{G'}$) of G'.

In another variation of this calibration method, the offsets of each of the three signals from the three accelerometers can be adjusted to better use the full range of A/D converter 110. In three parallel feedback loops, the X, Y and Z characteristics of the calculated value of G are used by offset feedback 170 to generate respectively three offsets to each of said signals, so that the input signals to A/D converter 110 are at the optimal point within the scale of A/D converter 110 when μ 342=0, for any orientation of G. The optimal point may be the mid-scale point of the A/D converter 110 for all three axes. Alternatively, any other suitable point(s) may be chosen, for example, the mid-scale point for the most horizontal axis, a −0.5 g offset for the middle axis, and a −1 g offset for the most vertical axis, since the maximum vertical acceleration with gravity is likely to be a free fall, but the maximum vertical acceleration against gravity can be several g's.

In an alternative embodiment, the EE of the system and the various components of EE can be calculated. FIG. 3 shows vector $\mu_v$ 344, which is the vertical component of the acceleration vector μ 342. $\mu_v$ 344 is the projection of μ 342 on G 332, and can be determined from μ and G using known trigonometric identities.

The magnitude of vector $\mu_v$ 344 ($\rho_{\mu v}$) can be used, together with the affected mass M, the gravity g, and the sampling interval t, to calculate the change in Potential Energy Expenditure ($EE_P$). In one variant of this method, a formula derived from the Newtonian work equation W=F·d can be used, assuming that $\rho_{\mu v}$ is constant over the sampling interval t, as follows:

$$EE_P = \tfrac{1}{2} \cdot M \cdot g \cdot \rho_{\mu v} \cdot t^2 \qquad (1)$$

Similarly, the magnitude of vector μ 342 ($\rho_\mu$) can be used, together with the affected mass M and the sampling interval t, to calculate the change in Kinetic Energy Expenditure ($EE_K$). In one variant of this method, a formula derived from the Newtonian work equation W=F·d can be used, assuming that $\rho_\mu$ is constant over the sampling interval t, as follows:

$$EE_K = \tfrac{1}{2} \cdot M \cdot \rho_\mu^2 \cdot t^2 \qquad (2)$$

It can be observed that the $EE_P$ formula (1) above is linear with $\rho_{\mu v}$, whereas the $EE_K$ formula (2) is quadratic with $\rho_\mu$. It can also be observed that $\mu_v$ contributes to both $EE_P$ and $EE_K$. In this and other variants of the method, separating out the estimation of $EE_P$ from $EE_K$ allows the different relationships between acceleration and EE to be derived and used for the various components of EE.

The Kinetic Energy Expenditure ($EE_K$) can be calculated independently for horizontal and vertical directions, using known trigonometric identities to calculate $\mu_H$ (where $\mu_H$ is the projection of μ on the horizontal plane normal to G), and by substituting $\mu_v$ and $\mu_H$ respectively for μ in Formula (2) above to calculate the horizontal and vertical components of $EE_K$.

In certain applications, the horizontal component of $EE_K$ can be further decomposed into component values corresponding to the horizontal projections of the anterior-posterior and medio-lateral axes of the user. This can be done, for example, by constraining the attachment of the device in known alignment with the anterior-posterior or medio-lateral axes of the user.

Figure 6A:
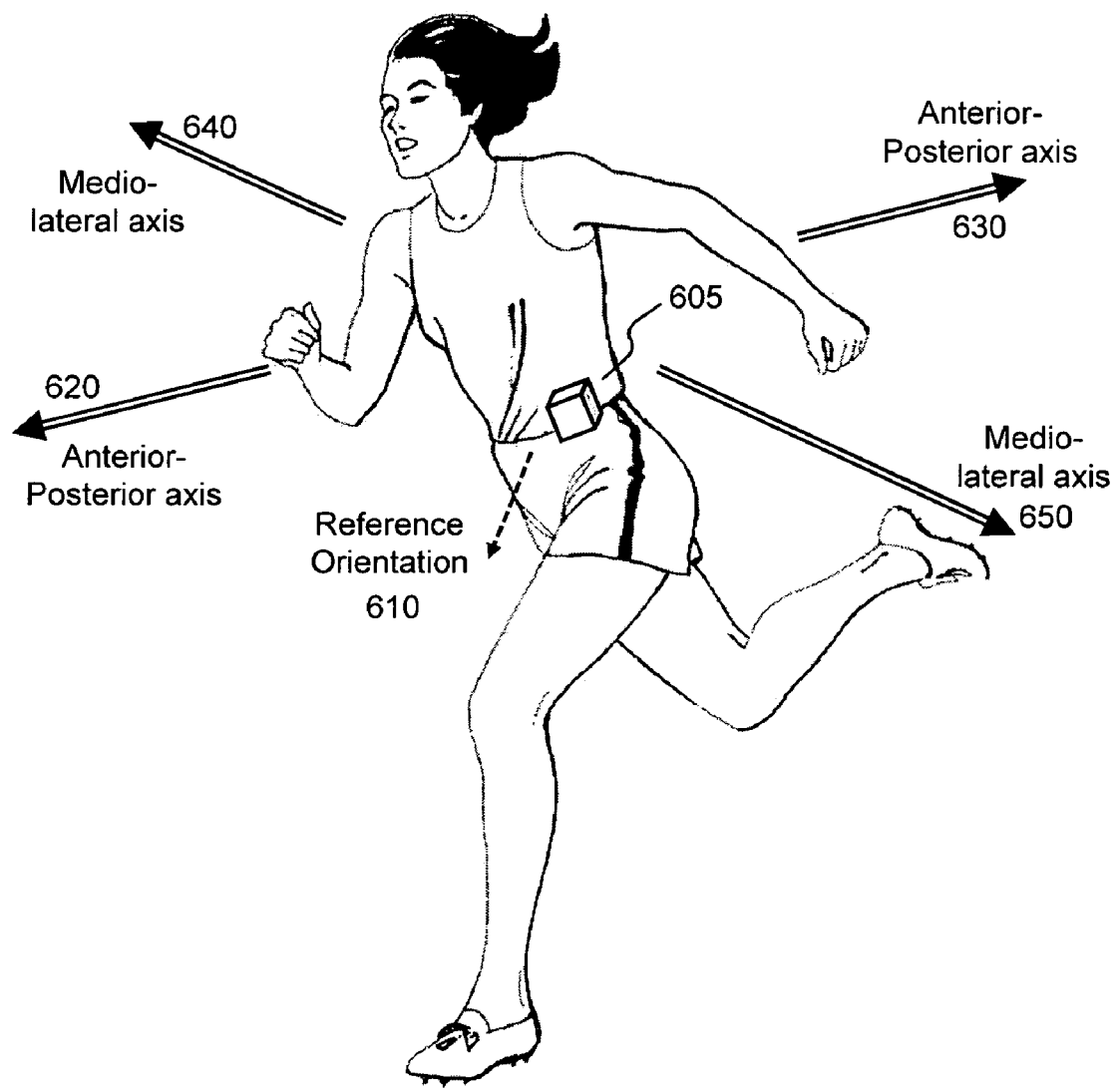
FIG. 6a is an illustration of a runner wearing an exemplary embodiment of a device according to this invention, showing certain axes of the runner and a reference orientation of the device.

FIG. 6a is an illustration of a runner wearing an exemplary embodiment of a device 605 according to the present invention. As shown in FIG. 6a, a reference orientation 610 is associated with the device 605. The reference orientation 610 can be aligned with one of the sensed acceleration axes 302, 304, 306 (see FIG. 3) of the device, or can be any other orientation that is defined with respect to the axes 302, 304, 306. The device 605 and its orientation 610 are independent of the axes of the runner, and thus the device 605 can be attached in any position and any orientation. In a preferred embodiment, the device is attached to the belt of the runner.

FIG. 6a also shows the projection of the runner's anterior-posterior axis 620, 630 and medio-lateral axis 640, 650 on the horizontal plane.

Figure 6B:
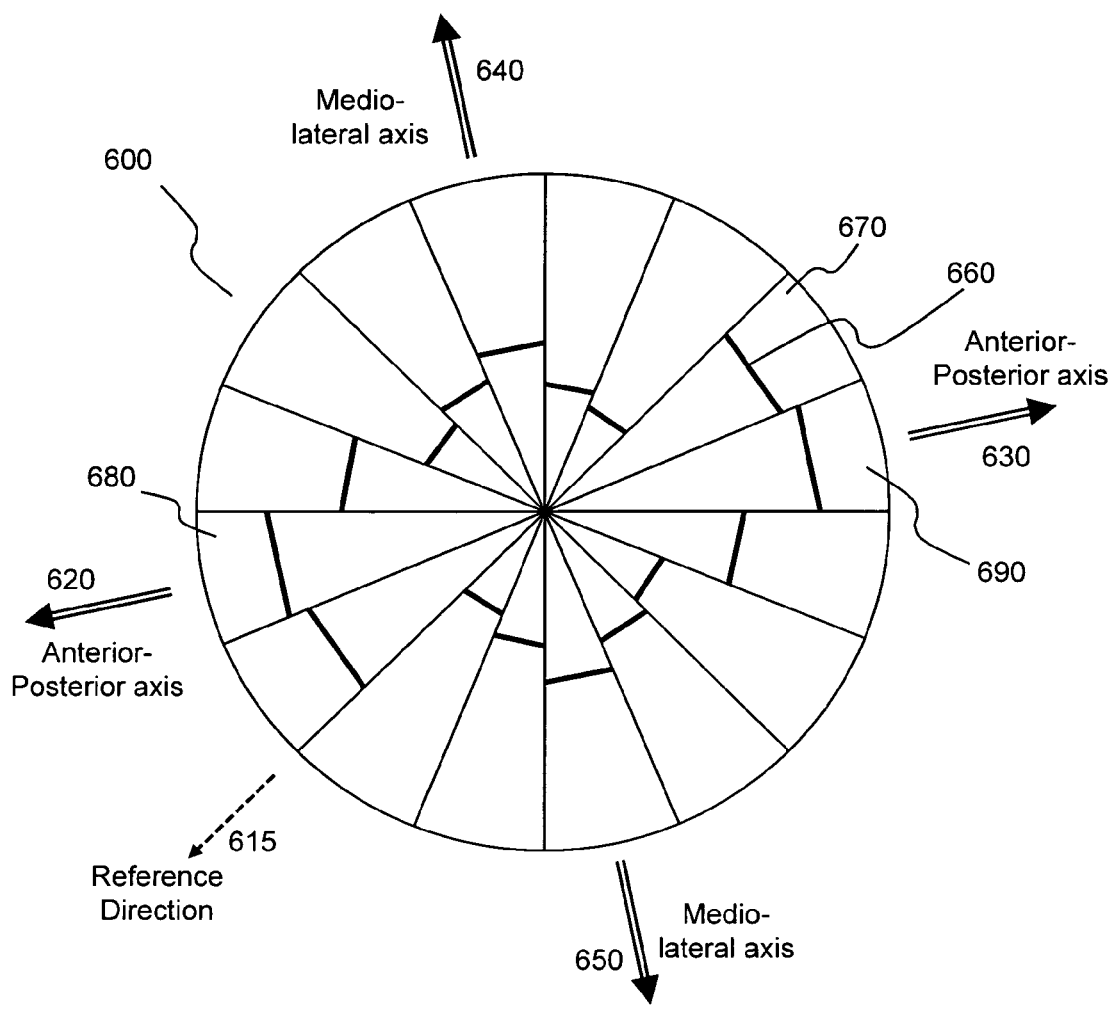

FIG. 6b is a geometric model 600 that illustrates a method, in accordance with the present invention, to distinguish the anterior-posterior axis 620, 630 from the medio-lateral axis 640, 650 in applications where the horizontal component of $EE_K$ peaks in one or more known directions, such as in the anterior-posterior direction for rowing or running, and if the attachment of the device 605 (see FIG. 6a) is not in known alignment with the anterior-posterior or medio-lateral axes of the user. Geometric model 600 is a plane, intersecting the origin of unit sphere 300 (see FIG. 3), and normal to the vector G 332 (see FIG. 3). Plane 600 is thus the horizontal plane.

In the embodiment shown in FIG. 6b, plane 600 has been divided into 16 equal sectors such as sector 670. In other embodiments, a larger or smaller number of sectors can be used. The sector boundaries are defined with respect to a reference direction 615, which is the projection of the reference orientation 610 of the device 605 on the horizontal plane 600. Reference orientation 610 can be arbitrarily chosen among available reference orientations of device 605 (such as any axis of device 605) to minimize the sensitivity of the reference direction 615 to changes in the gravity vector G 332, for example, by choosing a reference orientation 610 which is close to horizontal. During a period of physical activity, the accumulated horizontal component of $EE_K$ can be decomposed into sixteen horizontal directions, relative to reference direction 615, using known trigonometric identities. As shown in FIG. 6b, the magnitude of $EE_K$ in the direction of sector 670 is represented by the distance between the origin and line 660. The magnitude of $EE_K$ in the other fifteen directions is shown in a similar manner. In the example shown in FIG. 6b, $EE_K$ peaks approximately along an axis running inside sectors 680 and 690, with a secondary peak approximately at right angles to sectors 680 and 690, i.e., sectors 640 and 650. This pattern of a major peak in one direction and a secondary peak at right angles to the major peak is typical of the horizontal kinetic energy expenditure of a runner. If the physical activity is known a priori to be running, it is highly likely that components 680 and 690 are aligned with the anterior-posterior axis 620, 630 of the user, and thus $EE_K$ can be estimated for every direction relative to the user, without a-priori knowledge of the alignment between device 605 and the axes of the user.

These formulas (1), (2) for calculating $EE_P$, $EE_K$, the components of $EE_K$, and the total EE may be modified to compensate for the effects of human physiology, complex motion, affected mass, extremity motion, device attachment, friction, particular types of physical activity, or for other factors. For example, potential energy losses and kinetic energy gains can be ignored in environments where no autogenous energy is expended during periods of downward vertical motion in quasi-free fall. Additionally, a sample of individuals from a target population can be tested in a controlled environment, and the data can then be correlated to independent and simultaneous measures of actual energy expenditure, such as from oxygen consumption or doubly-labeled water. Using known statistical techniques, offset and scaling factors for the formulas (1), (2) that yield a best-fit correlation with the set of measured energy data points can be determined. The offset and scaling factors can then be used to modify the formulas (1), (2) and to provide improved measurement accuracy in subsequent use. Offset and scaling factors can be derived for the total EE or for any of its components or sub-components. Different offset and scaling factors for the various components can compensate for the difference in the effect of the various factors enumerated above on the different components of EE.

These formulas (1), (2) may also be modified by including posture data, posture patterns, or activity-type information, as additional variables in the correlation.

Values or patterns of the relationships between EE or its components, posture, and time can be used to analyze activity patterns, movement efficiency and impairment. One example is running efficiency. If a runner's anterior-posterior horizontal $EE_K$ contributes to moving her forward, and that runner's $EE_P$ and vertical $EE_K$ contribute primarily to up-and-down motion, then ratios of these energy expenditure components or any other suitable energy expenditure components may be related to running efficiency and may be used as immediate or time-delayed training feedback.

Another example is the amplitude or energy of postural swaying for low levels of EE compared to the amplitude or energy of postural swaying for high levels of EE, which may be of assistance in diagnosing mobility or balance impairments. Another example is comparing EE statistics over time, which may be of assistance in diagnosing changes in lifestyle or sedentary behavior. Another example is setting EE targets for an individual as part of a health maintenance or recovery program, and providing feedback on deviations from these targets. Another example is using posture or EE data to monitor a user's vital signs, a user's propensity to fall, a user's sleep patterns, or for workplace ergonomic studies and monitoring.

Figure 7:
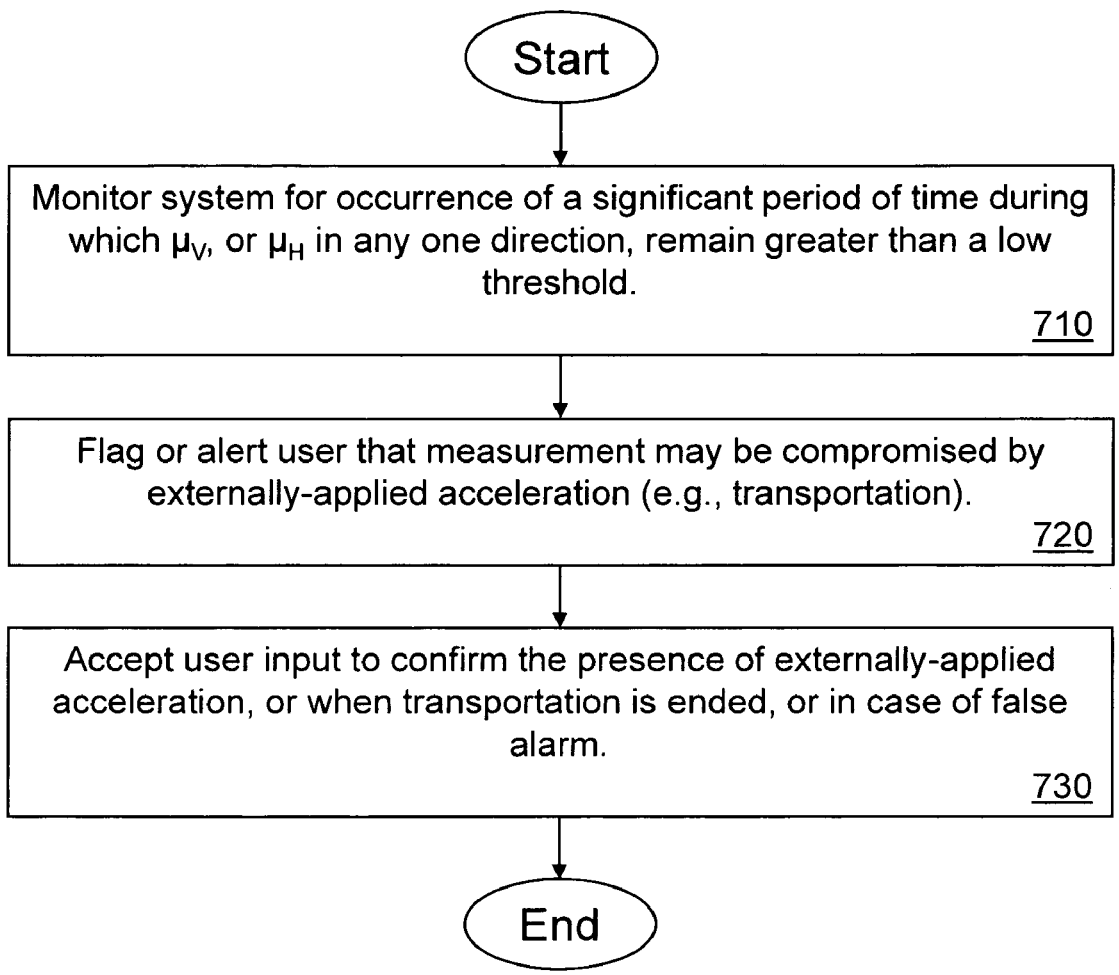
FIG. 7 is a flow diagram of a method of determining that the user is subject to externally-applied acceleration, typically caused by riding in a transportation vehicle.

FIG. 7 is a flow diagram depicting the operation of a system, in accordance with the present invention, which determines that the user is subjected to an externally-applied acceleration, such as is caused by traveling in an elevator, automobile, airplane, or other means of transportation. As depicted in step 710, the system is monitored for occurrence of a significant period of time (e.g., several seconds) during which $\mu_v$ remains greater than a low threshold (i.e., persistent acceleration against gravity). Under such conditions, it is highly likely that the user is being lifted upwards by an elevator or airplane. Similarly, the system is monitored for occurrence of a significant period of time (e.g., several seconds) during which $\mu_H$ in any one direction remains greater than a low threshold (i.e., persistent acceleration in any one horizontal direction). Under such conditions, it is highly likely that the user is being moved horizontally in an automobile or other form of transportation. Next, as depicted in step 720, the system flags the event or alerts the user that the measurement may be compromised by externally-applied acceleration. Finally, as depicted in step 730, the system accepts a user input to confirm the presence of the externally-caused acceleration, when the transportation is ended, or in the case of a false alarm.

In certain applications, these systems can be applied using an accelerometer with two sensing axes, if the wearer's motion is similarly limited to two directions. A runner, for example, moves her trunk in the vertical and anterior-posterior directions, but her trunk motion in the medio-lateral direction is limited. For such an application, a two-axis sensor whose sensor plane is aligned with the runner's sagittal plane can be used. The sagittal plane is a plane that divides the body into left and right portions.

In alternative embodiments, other sensing devices and/or techniques may be used along with or in place of accelerometers.

Systems that include these methods can also include one-way or two-way communication features. One example of a use of such a system is to remotely monitor an elderly person living by herself, to use posture or EE data to determine changes in health, mobility or lifestyle, and to use the communication features to communicate remotely with the individual.

It will be appreciated by those of ordinary skill in the art that modifications to and variations of the above-described system and method of performing posture and/or physical activity monitoring may be made without departing from the inventive concepts disclosed herein. Accordingly, the invention should not be viewed as limited except as by the scope and spirit of the appended claims.

What is claimed is:

1. An apparatus for monitoring posture and acceleration of a user, said apparatus being mountable to said user, comprising:
 a multi-axis sensor operative to sense gravity and acceleration along a plurality of axes by measuring a projection of an apparent gravity vector on each of said plurality of axes, said apparent gravity vector having a first component corresponding to an actual gravity vector and a second component corresponding to an acceleration vector, said actual gravity vector having a magnitude equal to 1 g;
 at least one memory operative to store data representative of the measured apparent gravity vector; and
 at least one processor operative to process the data stored in said at least one memory, said at least one processor being operative:
 to calculate a representation of the measured apparent gravity vector;
 to calculate, from said representation of the measured apparent gravity vector and said magnitude of said actual gravity vector, a representation of said actual gravity vector said actual gravity vector having an associated direction;
 to subtract said representation of said actual gravity vector from said representation of the measured apparent gravity vector to obtain a representation of said acceleration vector, said acceleration vector having an associated magnitude and an associated direction; and
 to generate at least one indication of one or more of the posture of said user based at least upon the direction of said actual gravity vector, and the acceleration of said user based at least upon the magnitude and the direction of said acceleration vector.

2. The apparatus of claim 1 wherein said at least one processor is further operative to calculate one or more of a vertical component of said acceleration vector and at least one horizontal component of said acceleration vector, wherein said calculation of said vertical component of said acceleration vector includes projecting said acceleration vector onto the actual gravity vector to obtain said vertical component, and wherein said calculation of said horizontal component of said acceleration vector includes projecting said acceleration vector onto a horizontal plane, said horizontal plane being normal to the actual gravity vector.

3. The apparatus of claim 1 wherein said apparent gravity vector has an associated direction, and wherein said apparatus further includes at least one first filter operative to filter the direction of said apparent gravity vector to generate at least one first filter output representing the direction of said actual gravity vector.

4. The apparatus of claim 3 wherein said apparent gravity vector has an associated magnitude, and wherein said apparatus further includes at least one second filter operative to filter the magnitude of said apparent gravity vector to generate at least one second filter output representing the magnitude of said actual gravity vector.

5. The apparatus of claim 4 wherein one or more of said at least one first filter and said at least one second filter are implemented within said at least one processor.

6. The apparatus of claim 4 wherein one or more of said at least one first filter and said at least one second filter have at least one adjustable coefficient, and wherein said at least one processor is further operative to adjust said at least one adjustable coefficient of one or more of said at least one first filter and said at least one second filter based upon at least one target value of at least one characteristic of at least one component of one or more of said actual gravity vector and said acceleration vector.

7. A method of monitoring posture and acceleration of a user, comprising the steps of:
 sensing, by a multi-axis sensor mounted to said user, gravity and acceleration along a plurality of axes,
 wherein said sensing of said gravity and said acceleration includes measuring a projection of an apparent gravity vector on each of said plurality of axes, said apparent gravity vector having a first component corresponding to an actual gravity vector, and a second component corresponding to an acceleration vector, said actual gravity vector having a magnitude equal to 1 g;
 calculating, by at least one processor, a representation of the measured apparent gravity vector;
 calculating, by said at least one processor from said representation of the measured apparent gravity vector and said magnitude of said actual gravity vector, a representation of said actual gravity vector, said actual gravity vector having an associated direction;
 subtracting, by said at least one processor, said representation of said actual gravity vector from said representation of the measured apparent gravity vector to obtain a representation of said acceleration vector, said acceleration vector having an associated magnitude and an associated direction; and
 generating at least one indication of one or more of the posture of said user based at least upon the direction of said actual gravity vector, and the acceleration of said user based at least upon the magnitude and the direction of said acceleration vector.

8. The method of claim 7 further including calculating at least one indication of one or more of a vertical component of said acceleration vector and at least one horizontal component of said acceleration vector, wherein said calculation of said vertical component of said acceleration vector includes projecting said acceleration vector onto the actual gravity vector to obtain said vertical component, and wherein said calculation of said horizontal component of said acceleration vector includes projecting said acceleration vector onto a horizontal plane, said horizontal plane being normal to the actual gravity vector.

9. The method of claim 7 wherein said apparent gravity vector has an associated direction, and wherein said method further includes filtering, by at least one first filter, the direction of said apparent gravity vector to generate at least one first filter output representing the direction of said actual gravity vector.

10. The method of claim 9 wherein said apparent gravity vector has an associated magnitude, and wherein said method further includes filtering, by at least one second filter, the magnitude of said apparent gravity vector to generate at least one second filter output representing the magnitude of said actual gravity vector.

11. The method of claim 10 wherein one or more of said at least one first filter and said at least one second filter have at least one adjustable coefficient, and wherein said method further includes adjusting said at least one adjustable coefficient of one or more of said at least one first filter and said at least one second filter based upon at least one target value of at least one characteristic of at least one component of one or more of said actual gravity vector and said acceleration vector.

12. A method of monitoring energy expended by a user, comprising the steps of:
    measuring, by a multi-axis sensor, an acceleration vector representing an acceleration of said user, said acceleration vector having an associated magnitude and a vertical component;
    calculating, by at least one processor, from the measured acceleration vector and a vector representing actual gravity, said vertical component of said acceleration vector, the actual gravity vector having an associated direction, said vertical component of said acceleration vector having an associated magnitude and an associated direction, the direction of said vertical component of said acceleration vector corresponding to the direction of the actual gravity vector;
    in a first calculating step, calculating, by said at least one processor, a first amount of energy expended by said user based upon the magnitude of said acceleration vector, said first amount of energy corresponding to a change in kinetic energy of said user;
    in a second calculating step, calculating, by said at least one processor, a second amount of energy expended by said user based upon the magnitude of said vertical component of said acceleration vector, said second amount of energy corresponding to a change in potential energy of said user; and
    generating an indication of an amount of total energy expended by said user based upon the calculated first and second amounts of energy.

13. The method of claim 12 further including determining at least one characteristic of motion of said user based at least in part upon one or more of said change in kinetic energy of said user and said change in potential energy of said user over a specified time interval.

14. The method of claim 12:
    wherein said vertical component has an associated direction;
    wherein said acceleration vector has at least one horizontal component;
    wherein said method further includes calculating, by said at least one processor, said at least one horizontal component of said acceleration vector, the horizontal component having an associated magnitude and an associated direction; and
    wherein said first calculating step includes:
        calculating said first amount of energy expended by said user based upon the magnitude of one or more of said vertical component and said at least one horizontal component of said acceleration vector, said first amount of energy corresponding to at least one change in kinetic energy of said user in the direction of one or more of said vertical component and said at least one horizontal component.

15. The method of claim 14 further including determining at least one characteristic of motion of said user based at least in part upon one or more of said change in kinetic energy of said user in the direction of one or more of said vertical component and said at least one horizontal component, and said change in potential energy of said user over a specified time interval.

16. The method of claim 12 wherein said calculating of said vertical component of said acceleration vector includes projecting said acceleration vector onto the actual gravity vector to obtain said vertical component.

17. A method of calibrating an accelerometer, said accelerometer including a multi-axis sensor, said method comprising the steps of:
    measuring, by said multi-axis sensor during a specified time interval, an apparent gravity vector to obtain a plurality of samples of said apparent gravity vector during said specified time interval, said apparent gravity vector having an associated magnitude and an associated direction,
    wherein at least one axis of said multi-axis sensor has at least one associated offset and at least one associated gain, one or more of the at least one offset and the at least one gain of the at least one axis of said multi-axis sensor being proportional to at least one adjustable parameter;
    calculating, by at least one processor, the magnitude and the direction of said apparent gravity vector;
    determining, from said plurality of samples of said apparent gravity vector, whether the magnitude and the direction of said apparent gravity vector are substantially unchanging during said specified time interval; and
    in the event the magnitude and the direction of said apparent gravity vector are substantially unchanging during said specified time interval, adjusting said at least one adjustable parameter to adjust one or more of the at least one offset and the at least one gain of the at least one axis of said multi-axis sensor, thereby setting one or more of the magnitude of said apparent gravity vector to a first specified value and the direction of said apparent gravity vector to a second specified value.

18. The method of claim 17 wherein said adjusting of said at least one adjustable parameter includes adjusting said at least one adjustable parameter to adjust one or more of the at least one offset and the at least one gain of the at least one axis of said multi-axis sensor, thereby setting the magnitude of the measured apparent gravity vector to 1 g.

19. The method of claim 17 further including, prior to said measuring of said apparent gravity vector, placing said multi-axis sensor in a predetermined reference position.

20. The method of claim 17 further including manipulating said multi-axis sensor through at least one sequence of one or more of at least one specified displacement and at least one specified rotation of said multi-axis sensor, said measuring of said apparent gravity vector being performed responsive to said at least one sequence of one or more of said at least one specified displacement and said at least one specified rotation of said multi-axis sensor.

21. A method of monitoring an externally applied acceleration of a user, comprising the steps of:
    measuring, by a multi-axis sensor, an acceleration vector representing an acceleration of said user, said acceleration vector having a vertical component and at least one horizontal component, each of said vertical component and said at least one horizontal component of said acceleration vector having an associated magnitude and an associated direction;
    calculating, by at least one processor from the measured acceleration vector and a vector representing actual gravity, said vertical component of said acceleration vector, the actual gravity vector having an associated direction, the direction of said vertical component of said acceleration vector corresponding to the direction of the actual gravity vector;

calculating, by said at least one processor, the horizontal component of the measured acceleration vector;

monitoring, during a specified time interval, one or more of the magnitude of said vertical component and the magnitude of the horizontal component of said acceleration vector; and in the event one or more of the magnitude of said vertical component and the magnitude of the horizontal component of said acceleration vector remain in excess of at least one specified threshold value during said specified time interval, generating at least one signal to indicate a presence of said externally applied acceleration.

22. The method of claim 21 further including receiving at least one user input to confirm one or more of said presence of said externally applied acceleration and an absence of said externally applied acceleration.

23. The method of claim 21 wherein said calculating of said vertical component of said acceleration vector includes projecting said acceleration vector onto the actual gravity vector to obtain said vertical component.

24. The method of claim 21 wherein said calculating of said horizontal component of said acceleration vector includes projecting said acceleration vector onto a horizontal plane, said horizontal plane being normal to the actual gravity vector.

25. A method of calibrating an accelerometer, said accelerometer including a multi-axis sensor, said method comprising the steps of:

measuring, by said multi-axis sensor, an apparent acceleration vector with reference to a plurality of axes to provide a plurality of analog sensor signals, each of said plurality of analog sensor signals representing a projection of said apparent acceleration vector onto a respective one of said plurality of axes, each of said plurality of analog sensor signals having an associated offset proportional to an adjustable parameter;

converting, by at least one analog-to-digital converter, each of the respective analog sensor signals to a corresponding digital sensor signal, the analog-to-digital converter having an associated conversion range; and for at least one of the respective analog sensor signals, adjusting said associated adjustable parameter to adjust the offset of the respective analog sensor signal so that the corresponding digital sensor signal lies within the conversion range of the respective analog-to-digital converter, wherein the corresponding digital sensor signal has a dynamic range based at least in part upon the adjusted offset of the respective analog sensor signal.

26. The method of claim 25 wherein said apparent acceleration vector has an associated magnitude, wherein the corresponding digital sensor signal has a digital value within a specified range of digital values, and wherein said adjusting of said at least one adjustable parameter includes adjusting said at least one adjustable parameter so that, in the event the magnitude of said apparent acceleration vector is equal to 1 g, the adjusted offset of the respective analog sensor signal causes said digital value to correspond to a predetermined digital value within said specified range of digital values.

27. A method of monitoring energy expended by a user in a plurality of horizontal directions during a specified time period and during performance of a specified activity, comprising the steps of:

measuring, by a sensor mounted to said user, an apparent acceleration vector;

calculating, by at least one processor, a gravity vector from the measured apparent acceleration vector;

subtracting, by said at least one processor, the calculated gravity vector from said apparent acceleration vector to obtain an actual acceleration vector, said actual acceleration vector representing an acceleration of said user;

defining a horizontal plane perpendicular to said gravity vector;

determining a reference direction relative to said sensor, said reference direction lying in said horizontal plane;

defining said plurality of horizontal directions relative to said reference direction of said sensor, said plurality of horizontal directions lying in said horizontal plane;

projecting, during said specified time period, said actual acceleration vector onto said horizontal plane in said plurality of horizontal directions; and calculating, by said at least one processor, a plurality of amounts of energy expended by said user in said plurality of horizontal directions based upon the projection of said actual acceleration vector onto said horizontal plane in said plurality of horizontal directions, each of said plurality of amounts of energy corresponding to a sum of changes in kinetic energy of said user in a respective one of said plurality of horizontal directions.

28. The method of claim 27 wherein said sensor has an associated axis defining a reference orientation of said sensor, and wherein said determining of said reference direction of said sensor includes determining a direction of a horizontal projection of said axis of said sensor on said horizontal plane.

29. The method of claim 28 further including choosing said reference orientation of said sensor among a plurality of possible reference orientations of said sensor such that the chosen reference orientation is substantially horizontal when said sensor is mounted on said user.

30. The method of claim 28 further including:

mounting said sensor to said user in such a manner that a value of an alignment offset between said reference orientation of said sensor and at least one axis of said user is known; and wherein said calculating of said plurality of amounts of energy expended by said user includes calculating, using the known value of said alignment offset, said plurality of amounts of energy expended by said user in a plurality of horizontal directions defined relative to said at least one axis of said user.

31. The method of claim 27:

wherein said plurality of amounts of energy expended by said user in said plurality of horizontal directions defines a pattern of energy expenditure for said specified activity, wherein said method further includes determining, based upon the defined pattern of energy expenditure for said specified activity, an approximate direction of a horizontal projection of at least one axis of said user on said horizontal plane; and wherein said calculating of said plurality of amounts of energy expended by said user includes calculating said plurality of amounts of energy expended by said user in a plurality of horizontal directions defined relative to said at least one axis of said user.

32. The method of claim 31 further including determining an alignment offset between said approximate direction of said horizontal projection of said at least one axis of said user and said reference direction of said sensor.

* * * * *

UNITED STATES PATENT AND TRADEMARK OFFICE
CERTIFICATE OF CORRECTION

PATENT NO. : 7,634,379 B2 Page 1 of 1
APPLICATION NO. : 12/077955
DATED : December 15, 2009
INVENTOR(S) : Christopher R. Noble It is certified that error appears in the above-identified patent and that said Letters Patent is hereby corrected as shown below:

Column 6, line 44, "p 342" should read --µ 342--.

Signed and Sealed this

Thirteenth Day of July, 2010

David J. Kappos
*Director of the United States Patent and Trademark Office*